United States Patent [19]

Finn

[11] Patent Number: 5,344,935
[45] Date of Patent: Sep. 6, 1994

[54] ALKYL ESTERS OF 5-HETEROCYCLIC-PYRIDINE-2,3-DICARBOXYLIC ACIDS AND METHODS FOR THE PREPARATION THEREOF

[75] Inventor: John M. Finn, Mercerville, N.J.

[73] Assignee: American Cyanamid Company, Wayne, N.J.

[21] Appl. No.: 68,363

[22] Filed: May 27, 1993

Related U.S. Application Data

[62] Division of Ser. No. 714,548, Jun. 11, 1991, Pat. No. 5,239,070, which is a division of Ser. No. 457,607, Dec. 27, 1989, Pat. No. 5,026,859.

[51] Int. Cl.⁵ .................. C07D 213/26; C07D 213/46; C07D 215/14
[52] U.S. Cl. .................................... 546/250; 546/168; 546/170
[58] Field of Search ................... 546/250, 170, 168

[56] References Cited

U.S. PATENT DOCUMENTS

| | | | |
|---|---|---|---|
| 4,638,068 | 1/1987 | Los | 71/66 |
| 4,758,667 | 1/1988 | Szczepanski et al. | 546/278 |
| 4,798,619 | 1/1989 | Los | 548/301 |

OTHER PUBLICATIONS

CA109(3):22968t Preparation of . . . herbicidal agents. Doehner p. 620, 1988.
CA113(13):115107j Preparation of . . . herbicide intermediates. Doehner, p. 675, 1990.
CA104(15):130206y Diels–Alder . . . nucleosides. Maggiora et al., 1986.

*Primary Examiner*—Mary C. Lee
*Assistant Examiner*—Joseph K. McKane
*Attorney, Agent, or Firm*—John W. Hogan, Jr.

[57] ABSTRACT

There are provided alkyl esters of 5-heterocyclic-pyridine-2,3-dicarboxylic acids useful as intermediates for the preparation of highly effective 5-heterocyclic-2-(2-imidazolin-2-yl)pyridine herbicidal agents and methods for the preparation thereof.

1 Claim, No Drawings

ALKYL ESTERS OF 5-HETEROCYCLIC-PYRIDINE-2,3-DICARBOXYLIC ACIDS AND METHODS FOR THE PREPARATION THEREOF

This is a divisional of co-pending application Ser. No. 07/714,548, filed on Jun. 11, 1991, now U.S. Pat. No. 5,239,070 in issue, which is a divisional of application Ser. No. 07/457,607 filed Dec. 27, 1989 now U.S. Pat. No. 5,026,859, issued Jun. 25, 1991.

BACKGROUND OF THE INVENTION

Imidazolinylpyridine and quinoline compounds, their use as herbicidal agents and methods for the preparation thereof are described in U.S. Pat. Nos. 4,638,068; 4,758,667 and 4,798,619. Quinoline carboxylates and dicarboxylates useful as intermediates in the preparation of herbicidal imidazolinyl quinoline compounds are described in U.S. Pat. No. 4,843,162.

It is an object of the present invention to provide 5-heterocyclic-pyridine-2,3-dicarboxylate esters useful as intermediates in the preparation of 5-heterocyclic-2-(2-imidazolin-2-yl)pyridine herbicidal agents and processes for the preparation thereof.

SUMMARY OF THE INVENTION

The present invention relates to 5-heterocyclic-pyridine-2,3-dicarboxylates having the structure

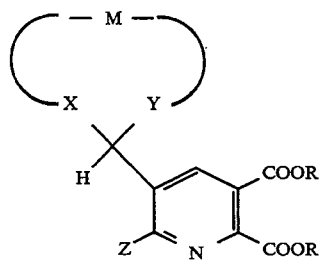

(I)

wherein

R is $C_1$–$C_6$ alkyl;

X and Y are each independently oxygen, sulfur or $NR_4$;

$R_4$ is hydrogen, $C_1$–$C_6$ alkyl optionally substituted with $C_1$–$C_4$ alkoxy or 1–3 halogens, $SO_2R_5$, $COR_5$, $CO_2R_5$ or $CONR_5R_5$;

$R_5$ is hydrogen, $C_1$–$C_6$ alkyl optionally substituted with 1–3 halogens, or $C_2$–$C_6$ alkenyl;

M is $C_2$–$C_5$ alkylene optionally substituted with 1 or 2 $C_1$–$C_4$ alkyl groups, $C_1$–$C_4$ alkoxy, halogen, $CO_2R_6$ or oxo, and optionally interrupted by one oxygen or one sulfur, $C_2$ alkenylene optionally substituted with 1 or 2 $C_1$–$C_4$ alkyl groups or $CO_2R_6$, $C_3$ alkenylene optionally substituted with 1 or 2 $C_1$–$C_4$ alkyl groups, $CO_2R_6$ or oxo, methyleneamino, optionally substituted with $C_1$–$C_4$ alkyl or $CO_2R_6$, or a single bond, with the proviso that both X and Y are $NR_4$, provided that the ring formed by M, X and Y and the carbon to which they are attached is no more than 8 atoms and provided that when the substituents on M are either alkoxy or halogen the substituted carbon is not bound to X or Y;

$R_6$ is hydrogen, methyl or ethyl;

Z is hydrogen, halogen, $C_1$–$C_6$ alkoxy, or $C_1$–$C_6$ alkyl optionally substituted with $C_1$–$C_4$ alkoxy or halogen.

The compounds of the present invention are useful as intermediates in the preparation of highly effective 5-heterocyclic-2-(2-imidazolin-2-yl)pyridine herbicidal agents. Said 5-heterocyclic-2-(2-imidazolin-2-yl)pyridine compounds and their herbicidal use are described in co-pending U.S. patent application Ser. No. 07/457,606, now U.S. Pat. No. 5,039,333, filed concurrently herewith and incorporated herein by reference thereto.

DESCRIPTION OF THE INVENTION

The present invention relates to 5-heterocyclic-pyridine-2,3-dicarboxylate compounds of having the formula I structure

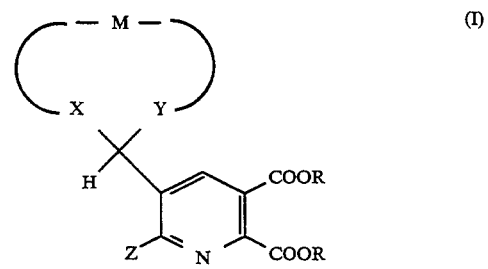

(I)

wherein

R is $C_1$–$C_6$ alkyl;

X and Y are each independently oxygen, sulfur or $NR_4$;

$R_4$ is hydrogen, $C_1$–$C_6$ alkyl optionally substituted with $C_1$–$C_4$ alkoxy or 1–3 halogens, $SO_2R_5$, $COR_5$, $CO_2R_5$ or $CONR_5R_5$;

$R_5$ is hydrogen, $C_1$–$C_6$ alkyl optionally substituted with 1–3 halogens, or $C_2$–$C_6$ alkenyl;

M is $C_2$–$C_5$ alkylene optionally substituted with 1 or 2 $C_1$–$C_4$ alkyl groups, $C_1$–$C_4$ alkoxy, halogen, $CO_2R_6$ or oxo, and optionally interrupted by one oxygen or one sulfur, $C_2$ alkenylene optionally substituted with 1 or 2 $C_1$–$C_4$ alkyl groups or $CO_2R_6$, $C_3$ alkenylene optionally substituted with 1 or 2 $C_1$–$C_4$ alkyl groups, $CO_2R_6$ or oxo, methyleneamino, optionally substituted with $C_1$–$C_4$ alkyl or $CO_2R_6$, or a single bond, with the proviso that both X and Y are $NR_4$, provided that the ring formed by M, X and Y and the carbon to which they are attached is no more than 8 atoms and provided that when the substituents on M are either alkoxy or halogen the substituted carbon is not bound to X or Y;

$R_6$ is hydrogen, methyl or ethyl;

Z is hydrogen, halogen, $C_1$–$C_6$ alkoxy, or $C_1$–$C_6$ alkyl optionally substituted with $C_1$–$C_4$ alkoxy or halogen.

The 5-heterocyclic-pyridinedicarboxylates of the present invention are important intermediates in the preparation of highly effective 5-heterocyclic-2-(2-imidazolin-2-yl)pyridine herbicidal agents of formula II.

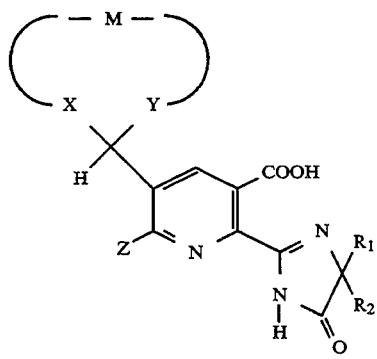

(II)

wherein
R₁ is $C_1$-$C_4$ alkyl;
R₂ is $C_1$-$C_4$ alkyl or $C_3$-$C_6$ cycloalkyl and when R₁ and R₂ are taken together with the carbon to which they are attached they may represent $C_3$-$C_6$ cycloalkyl;
Z, X, M and Y are as described above for formula I.

Conversion of the formula I 5]heterocyclic-pyridine diesters of the present invention to the highly effective herbicidal agents of formula II is achieved by the reaction of the formula I 5-heterocyclic-2,3-pyridinedicarboxylate ester with an aminocarboxamide having the structure

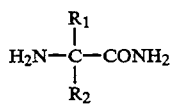

in the presence of a base, such as an alkali metal butoxide, and a solvent followed by treatment with an aqueous acid. The conversion is shown in Flow Diagram I.

Flow Diagram I

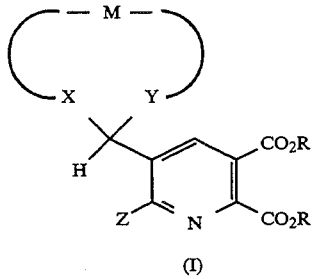

Alternatively, the compounds of the present invention may be utilized to prepare herbicidal agents of formula II by saponifing the formula I pyridinedicarboxylate to obtain the corresponding dicarboxylic acid (formula III), reacting said formula III dicarboxylic acid with acetic anhydride to obtain the corresponding anhydride of formula IV, reacting the formula IV anhydride with at least one equivalent of an aminocarboxamide in the presence of a base to yield an intermediate having the structural formula V and reacting said formula V intermediate sequentially with a strong base and an aqueous acid to give the herbicidal formula II compound as illustrated below in Flow Diagram II.

Flow Diagram II

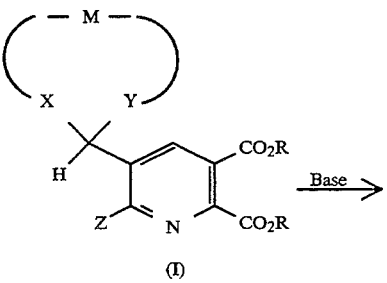

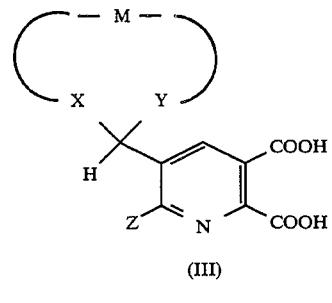

-continued
Flow Diagram II

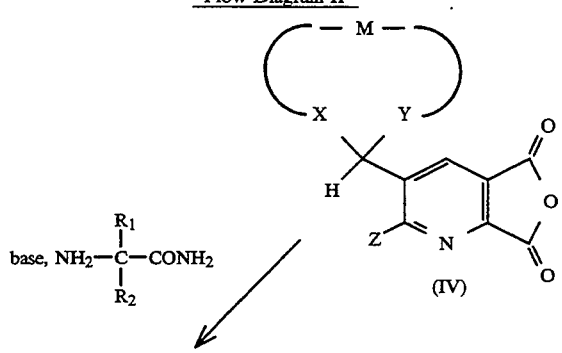

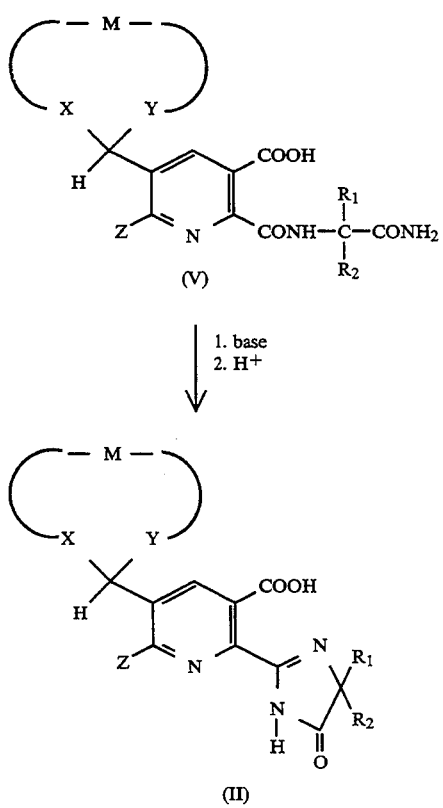

In accordance with the process of the present invention the versatile compounds of formula I are prepared by the esterification and halogenation of 5-methyl-2,3-pyridinedicarboxylic acid to yield both a 5-(dihalomethyl)-2,3-pyridinedicarboxylate first intermediate having the structural formula VI and a 5-halomethyl)-2,3-pyridinedicarboxylate second intermediate of formula VII, reaction of the formula VI, first intermediate with a ($C_1$–$C_4$)alkyl alcohol and at least 2 equivalents of silver nitrate to give a 5-formyl-2,3-pyridinedicarboxylate, 5-di($C_1$–$C_4$)alkyl acetal of formula VIII and reaction of said formula VIII acetal with an agent having the structural formula IX $$HX-M-YH \qquad (IX)$$

wherein M, X and Y are as described above for formula I in the presence of a catalytic amount of an acid and a solvent gives the formula I 5-heterocyclic-pyridinedicarboxylate compound. Alternatively, the formula VI first intermediate is reacted with at least 2 equivalents of aqueous silver nitrate to yield a 5-formyl-2,3-pyridinedicarboxylate of formula X and the formula X compound is reacted with a formula IX agent as described above to give the desired formula I compound. Similarly, the formula VII 5-(halomethyl)-2,3-pyridinedicarboxylate is readily converted to the formula X 5-formyl-2,3-pyridinedicarboxylate by reacting said formula VII diester with silver tetrafluoroborate in the presence of dimethyl sulfoxide. Additionally, the formula VI first intermediate is directly converted to the desired 5-heterocyclic-pyridine-2,3-dicarboxylate of formula I by reacting said formula VI compound with a formula IX agent in the presence of silver nitrate and a solvent. The reaction processes are illustrated in Flow Diagram III.

Flow Diagram III

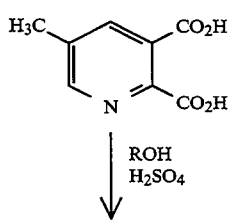

Flow Diagram III

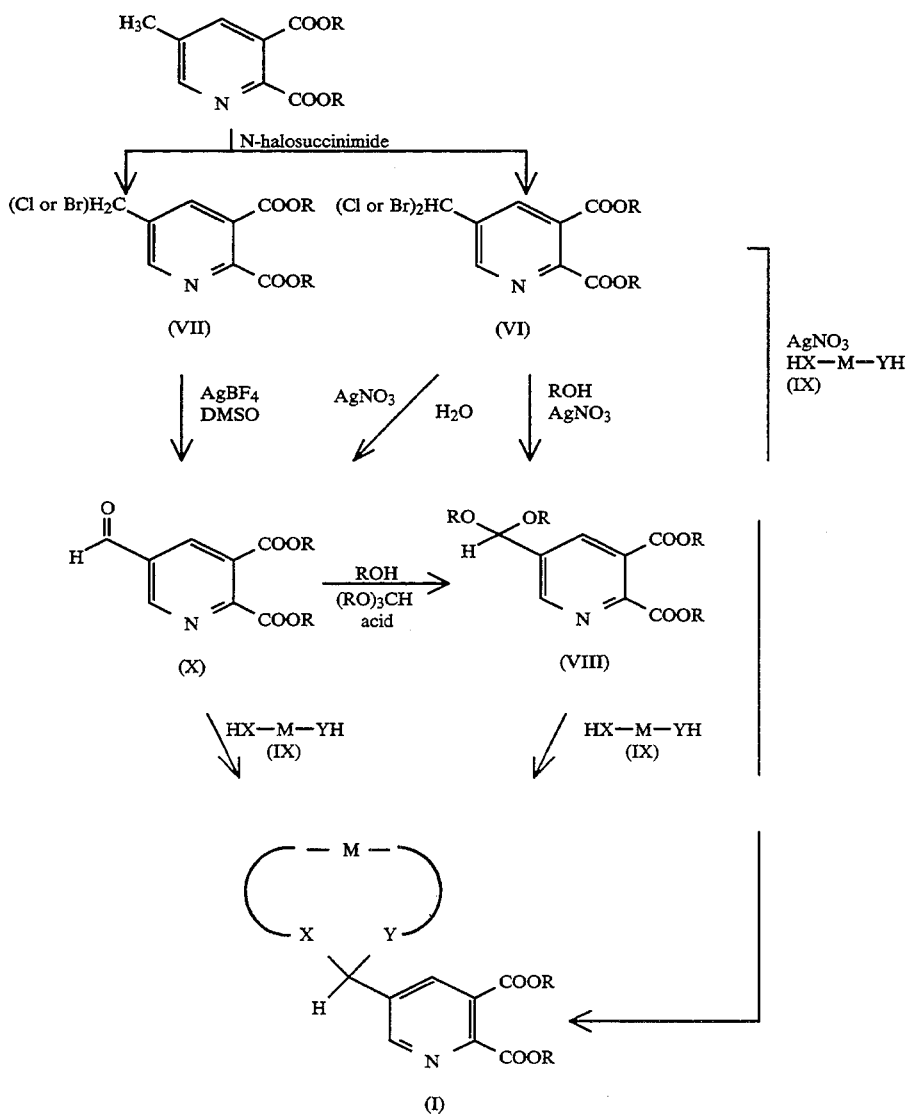

A further process of the invention is the reaction of a 2′,5′-diloweralkoxyacetanilide of formula XI with phosphorous oxychloride and dimethylformamide to give a 2-chloro-5,8-diloweralkoxyquinolinecarboxaldehyde of formula XII which is advantageously converted to the formula XIII 5-acetal-6-chloropyridinedicarboxylate intermediate in a single step by the reaction of said formula XII quinoline carboxaldehyde with ozone, at least 2 equivalents of triloweralkylorthoformate and a loweralkyl alcohol in the presence of a mineral acid to yield the formula XIII pyridinedicarboxylate which is converted to the desired formula I product, wherein Z is chlorine, by the reaction of said formula XIII compound with a formula IX agent as described hereinabove. The formula XII quinolinecarboxaldehyde is also obtained by reacting a formula IV β-anilino-α,β-unsaturated ester with phosphorous oxychloride and dimethylformamide to give the formula XV 2-chloro-3-quinolinecarboxylate and sequentially reacting said formula XV carboxylate with lithium aluminum hydride (LAH) and pyridinium chlorochromate (PCC) to give the corresponding formula XII quinolinecarboxaldehyde. Compounds of formula I wherein Z is chlorine may be converted to compounds of formula I wherein Z is hydrogen via catalytic hydrogenation. The above-described processes are illustrated in Flow Diagram IV.

Flow Diagram IV

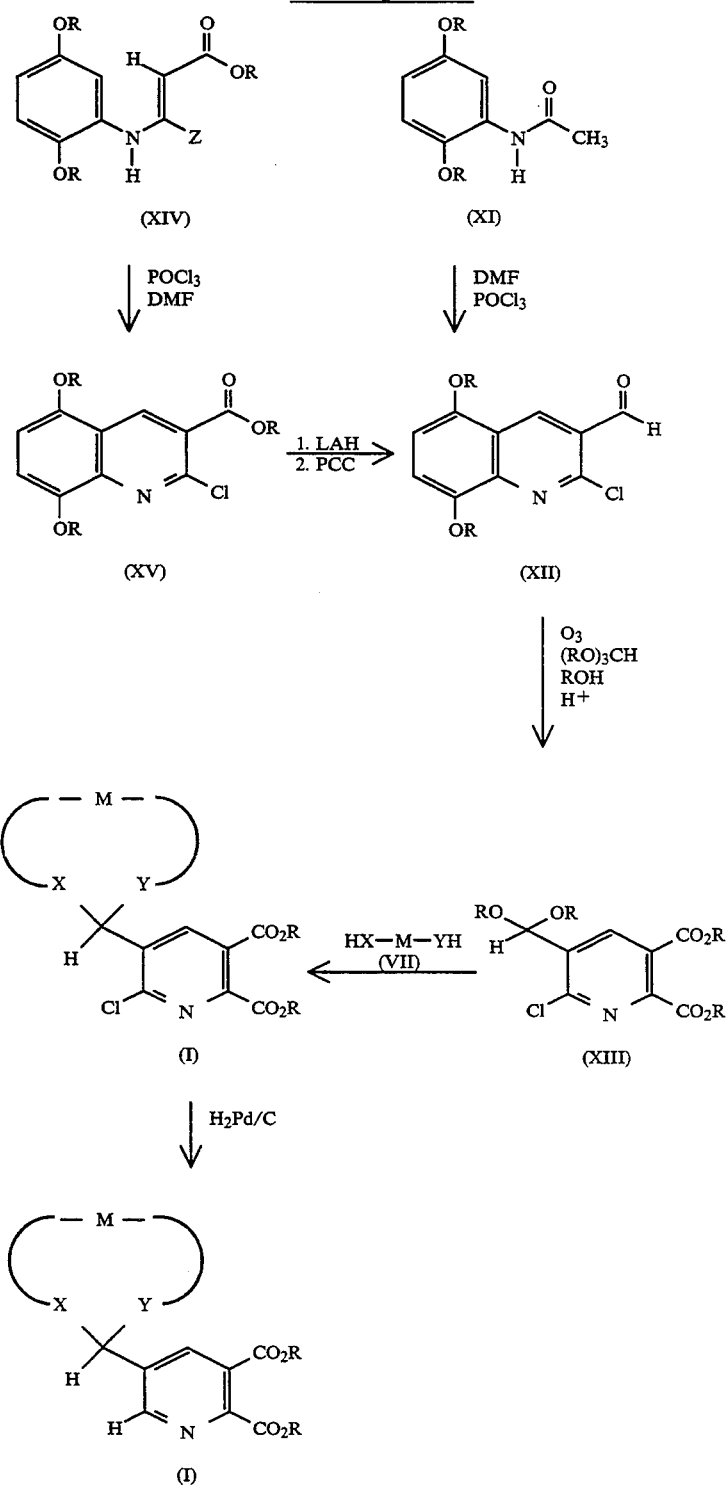

Formula I compounds of the present invention wherein Z is $C_1$–$C_6$ alkoxy are prepared by converting the intermediate acetal of formula XIII to the corresponding 5-formylpyridinedicarboxylate of formula XVI, reacting said formula XVI compound with an alkali metal $C_1$–$C_6$ alkoxide to obtain the 6-alkoxypyridine of formula XVII and reacting said formula XVII compound with a formula IX agent as described hereinabove to obtain the desired formula I compound wherein Z is $C_1$–$C_6$ alkoxy. This reaction sequence is illustrated in Flow Diagram V Flow Diagram V

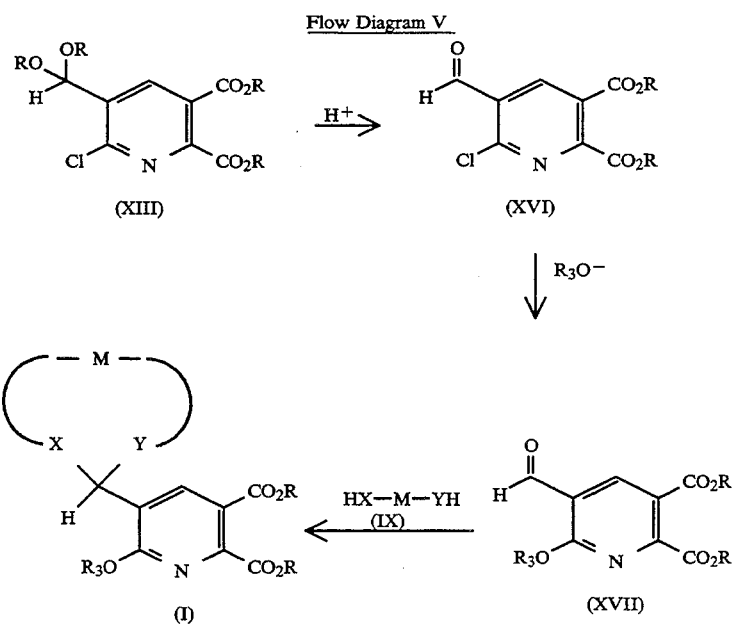

wherein $R_3$ is $C_1$–$C_6$ alkyl.

In order to facilitate a further understanding of the invention, the following examples are presented primarily for the purpose of illustrating more specific details thereof. The invention is not to be deemed limited thereby except as defined in the claims. IR and NMR designate infrared and proton nuclear magnetic resonance, respectively.

EXAMPLE 1

Preparation of Dimethyl 5-(dibromomethyl)-2,3-pyridinedicarboxylate And Dimethyl 5-(bromomethyl)2,3 -pyridinedicarboxylate

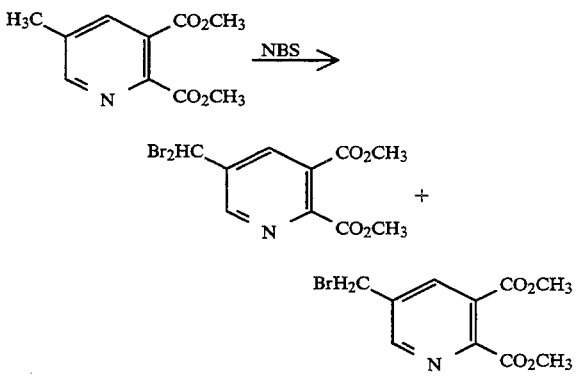

N-bromosuccinimide (83.06 g, 0.46 mol) and benzoyl peroxide (11.28 g, 0.046 mol) are added, in 5 portions over a 7 hour period, to a solution of 5-methyl-2,3-pyridinedicarboxylic acid, dimethyl ester (42.5 g, 0.20 mol) in carbon tetrachloride heated at reflux temperature. The reaction mixture is heated at reflux temperature for 2 hours, cooled to room temperature, filtered and the solids are washed with methylene chloride. The filtrate is washed sequentially with 5% sodium metabisulfite solution and 5% sodium bicarbonate solution, dried over anhydrous magnesium sulfate and concentrated in vacuo to give an oil. The oil is chromatographed on silica gel using 16% ethyl acetate in hexanes and 33% ethyl acetate in hexanes as eluant to give dimethyl 5-(dibromomethyl)-2-3-pyridinedicarboxylate as a white solid, (47.2 g, 64%), mp 61°-65° C., identified by IR and NMR spectral analyses and dimethyl 5-(bromomethyl)2,3-pyridinedicarboxylate (11.4, 20%) as a clear oil, identified by IR and NMR spectral analyses.

EXAMPLE 2

Preparation of Ethyl 3-(2,5-dimethylanilino)crotonate

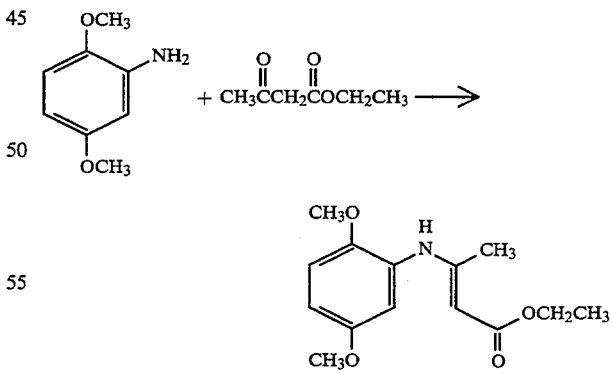

A solution of 2,5-dimethoxyaniline (80 g, 0.52 mol) and ethyl acetoacetate (66 mL, 0.52 mol) in toluene (200 mL) and acetic acid (2 mL) is stirred at reflux temperature for 6 hours. The reaction mixture is concentrated in vacuo and the crude product is purified by chromatography using silica gel and ethyl acetate in hexanes as eluant to yield the title compound (7.32 g, 12%) as a white solid mp 67° C. identified by IR and NMR spectral analyses.

EXAMPLE 3

Preparation of Ethyl 5,8-Dimethoxy-2-methylquinoline-3-carboxylate

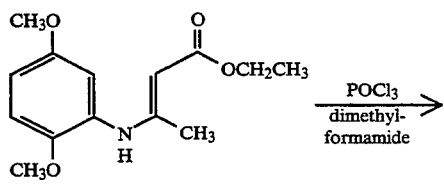

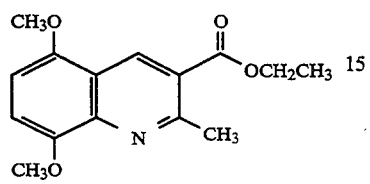

To a 0° C. solution of dimethylformamide (7.5 mL, 0.097 mol) in dichloroethane (20 mL) is added dropwise phosphorous oxychloride (9.0 mL, 0.097 mol). After stirring for 3.5 hours at room temperature, a solution of ethyl 3-(2,5-dimethoxyanilino)crotonate (25.8 g, 0.097 mol) in dichloroethane (130 mL) is added dropwise at 25° C. The resulting solution is heated at reflux temperature for 3 hours. After cooling to room temperature, the reaction is quenched by the addition of an aqueous ammonium chloride solution. Methylene chloride (200 mL) is added and the layers are separated. The organic layer is dried over anhydrous magnesium sulfate and concentrated in vacuo to give a residue. The residue is purified by chromatography using silica gel and ethyl acetate in hexanes as eluant to yield the title compound (34 g, 100%) as a yellow solid identified by IR and NMR spectral analyses.

EXAMPLE 4

Preparation of 5,8-Dimethoxy-3-formyl-2-methylquinoline

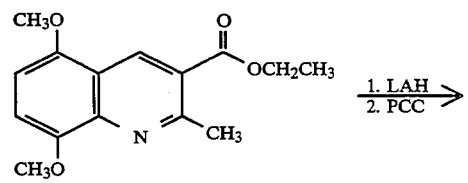

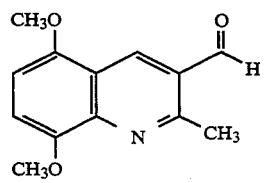

A solution of ethyl 5,8-dimethoxy-2-methylquinoline-3-carboxylate (4.0 g, 0.0145 mol) in tetrahydrofuran is added to a slurry of lithium aluminum hydride (0.72 g, 0,019 mol) in ether. The reaction is stirred for 16 hours at 50° C. After cooling, the reaction is quenched by the sequential addition of water and 15% aqueous sodium hydroxide. Additional ether and anhydrous magnesium sulfate are added and the reaction mixture is filtered. The product is purified by chromatography using silica gel and ethyl acetate in hexanes as eluant. The resulting alcohol (1.50 g) is dissolved in methylene chloride and added to a slurry of pyridinium chlorochromate in methylene chloride. The resulting solution is stirred for 3 hours at room temperature. Diatomaceous earth is added, the reaction mixture is diluted with ether and filtered. The filtrate is concentrated in vacuo and the product purified by chromatography using silica gel and ethyl acetate in hexanes as eluant to yield the title compound (0.10 g, 5%) as a yellow solid, identified by IR and NMR spectral analysis.

EXAMPLE 5

Preparation of 2-Chloro-5,8-dimethoxy-3-quinolinecarboxaldehyde

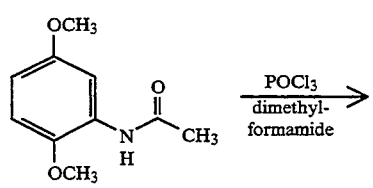

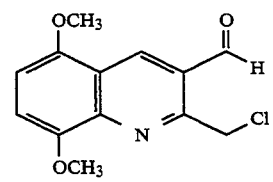

To a 0° C. solution of dimethylformamide (80 mL, 1.04 mol) is added phosphorus oxychloride (250 mL, 2.7 mol). The reaction mixture is heated at 50° C. for 45 minutes, then solid 2',5'-dimethoxyacetanilide (93.62 g, 0.48 mol) is added. The reaction mixture is heated for 4.5 hours at 75° C., cooled to room temperature, quenched with water and ice, stirred for 3 hours and 30 minutes and filtered to give a solid. The solid is recrystallized from ethyl acetate to yield the title compound as a yellow powder (13.64 g, 11%), mp 177°–178° C., identified by IR and NMR spectral analyses.

EXAMPLE 6

Preparation of Dimethyl 6-chloro-5-formyl-2,3-pyridinedicarboxylate, 5-(dimethyl acetal)

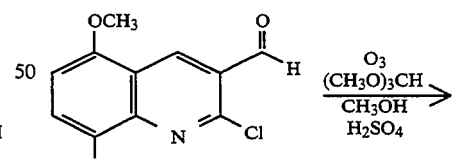

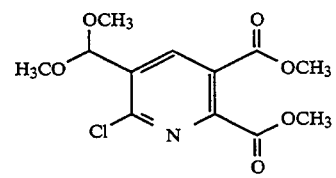

To a solution of 2-chloro-5,8-dimethoxy-3-quinolinecarboxaldehyde (27.32 g, 0.11 mol) and methanol is added trimethylorthoformate (86 mL, 0.785 mol) and concentrated sulfuric acid (2 mL). Ozone is then bubbled through the reaction mixture for a total of 11 hours. Concentration in vacuo yields an oil which is dissolved into ether, washed sequentially with saturated sodium bicarbonate solution, saturated sodium metabisulfite solution and brine. The solution is dried over anhydrous magnesium sulfate and concentrated in vacuo to yield the title compound as an orange oil (20.13 g, 61%), identified by IR and NMR spectral analyses.

Following the above procedure and employing the appropriately substituted quinoline carboxaldehyde the following compounds are obtained.

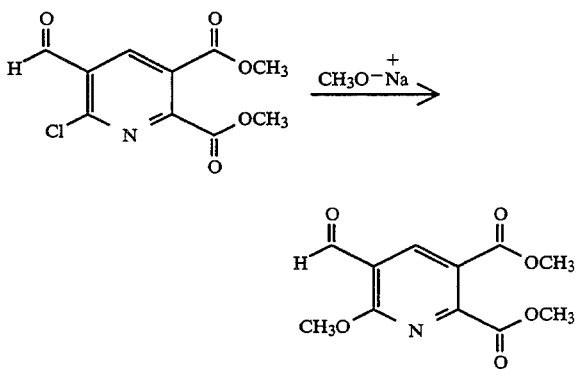

| Z | mp |
|---|---|
| $CH_3$ | oil |
| Cl | oil |
| $CH_2CH_3$ | |
| $OCH_3$ | |
| $OCH_2CH_3$ | |
| Br | |

EXAMPLE 7

Preparation of Dimethyl 5-formylpyridine-2,3-dicarboxylate

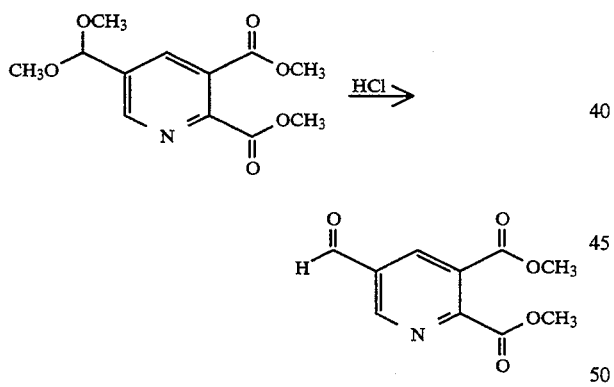

A solution of dimethyl 5-dimethoxymethylpyridine-2,3-dicarboxylate (6.57 g, 0.024 mol) in 2N HCl (15 mL) and tetrahydrofuran (25 mL) is stirred at reflux temperature for 2 hours. The tetrahydrofuran is removed in vacuo, the aqueous solution is diluted with water (to 30 mL) and extracted with methylene chloride. The combined methylene chloride extracts are dried over anhydrous magnesium sulfate and concentrated in vacuo to yield the title compound (4.51 g, 82%) as a yellow solid, mp 75°-77° C., identified by IR and NMR spectral analyses.

Using the above procedure and employing dimethyl 5-dimethoxymethyl-6-chloropyridine-2,3-dicarboxylate as starting material affords dimethyl 5-formyl-6-chloropyridine-2,3-dicarboxylate as an oil.

EXAMPLE 8

Preparation of Dimethyl 5-formyl-6-methoxyridine-2,3-dicarboxylate

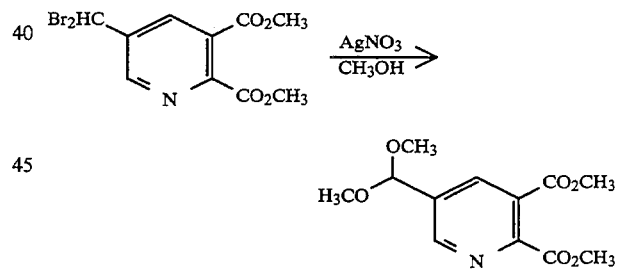

A solution of dimethyl 6-chloro-5-formylpyridine-2,3-dicarboxylate (1.0 g, 0.0039 mol) in methanol (10 mL) is added to sodium methoxide (0.42 g, 0.0078 mol) in methanol (2 mL). The resulting mixture is stirred for 15 hours at 90° C. After cooling to room temperature, the reaction mixture is acidified to pH 3.0 with acetic acid. The reaction is poured into methylene chloride, washed with water, dried over anhydrous magnesium sulfate and concentrated in vacuo to yield the title compound (0.62 g, 63%) as an orange oil, identified by IR and NMR spectral analyses.

EXAMPLE 9

Preparation of Dimethyl 5-formyl-2,3-pyridinedicarboxylate, 5-dimethyl acetal

Silver nitrate (134.49 g, 0.816 mol) is added to a solution of 5-(dibromomethyl)-2,3-pyridinedicarboxylic acid, dimethyl ester (146.01 g, 0.398 mol) and methanol. The reaction mixture is stirred for 30 minutes at 25° C. then for 1 hour and 30 minutes at reflux temperature. The reaction mixture is cooled to room temperature, filtered through a pad of diatomaceous earth and the diatomaceous earth is rinsed with methanol. The filtrate is concentrated in vacuo to give an oil. The oil is dissolved in methylene chloride, washed with 5% sodium bicarbonate solution, dried over anhydrous magnesium sulfate and concentrated in vacuo to give an oil. The residue oil is chromatographed using silica gel, 16% ethyl acetate in hexanes and 50% ethyl acetate in hexanes as eluant to yield the title compound as a clear oil, (98.39 g, 92%), identified by IR and NMR spectral analyses.

EXAMPLE 10

Preparation of Dimethyl 5-dimethoxymethylpyridine-2,3-dicarboxylate

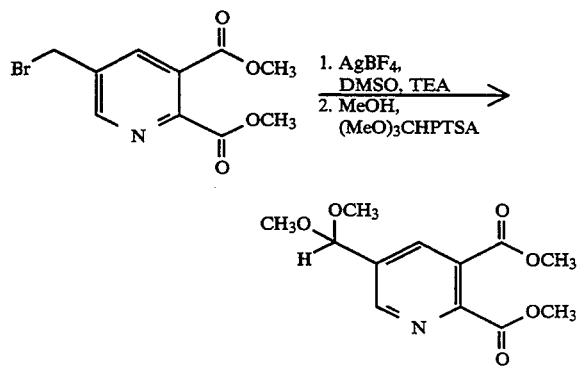

To a solution of dimethyl 5-bromomethylpyridine-2,3-dicarboxylate (10.55 g, 0.0366 mol) in dimethylsulfoxide (50 mL) is added solid silver tetrafluoroborate (8.91 g, 0.0458 mol). The resulting mixture is stirred for 1.5 hours at 80°–90° C., then triethylamine (6.75 mL 0,458 mol) is added and the reaction mixture is stirred for an additional 1 hour at 80° C. The reaction is filtered through a pad of diatomaceous earth and the diatomaceous earth is rinsed with methanol. The filtrate is concentrated in vacuo and the crude product is dissolved in methanol (100 mL) and trimethylorthoformate (15 mL). A catalytic amount of para-toluenesulfonic acid is added and the reaction mixture is stirred at reflux temperature for 4.5 days. The reaction mixture is concentrated in vacuo and diluted with H$_2$O and passed through a pad of C-18 silica gel. Elution with methanol in water affords a crude product, which is purified by chromatography on silica gel using ethyl acetate in hexanes as eluant to yield the title compound (1.96 g, 20%) as a clear oil, identified by IR and NMR spectral analyses.

EXAMPLE 11

Preparation of Dimethyl 5-formylpyridine-2,3-dicarboxylate

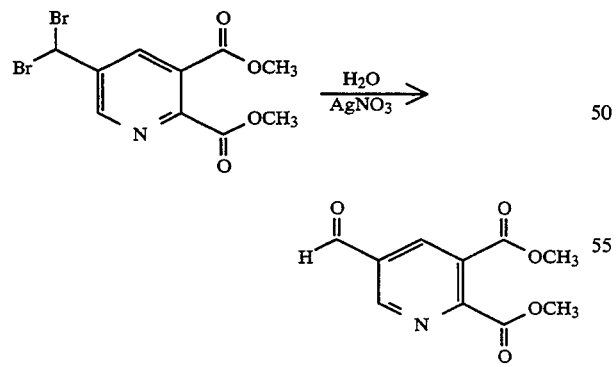

To a solution of dimethyl 5-dibromomethylpyridine-2,3-dicarboxylate (8.32 g, 0.0227 mol) in dioxane (60 mL) and water (20 mL) is added silver nitrate (7.85 g, 0.0476 mol). The resulting slurry is heated at reflux for 3 hours. The reaction mixture is cooled to room temperature, filtered through a pad of diatomaceous earth and the diatomaceous earth is rinsed with tetrahydrofuran. The filtrate is concentrated in vacuo to remove the dioxane and tetrahydrofuran. The resultant aqueous solution is made basic by the addition to saturated aqueous sodium bicarbonate (100 mL) and extracted with methylene dichloride. The combined extracts are dried over anhydrous magnesium sulfate and concentrated in vacuo to give a residue. Chromatography using silica gel and 33% ethyl acetate in hexanes as eluant yields the title compound as a white solid, (4.31 g, 85%) mp 75° C.–77° C., identified by IR and NMR spectral analyses.

EXAMPLE 12

Preparation of 5-Formyl-2-(4-isopropyl-4-methyl-5-oxo-2-imidazolin-2-yl)nicotinic acid 5-(dimethyl acetal)

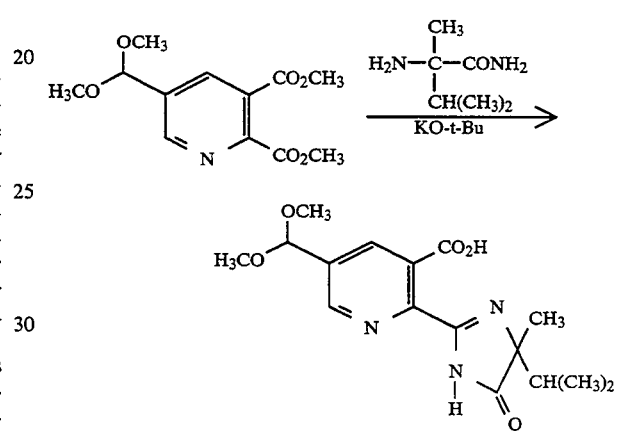

Potassium tert-butoxide (26.55 g, 0,236 mol) is added portionwise to a stirred solution of 5-formyl-2,3-pyridinedicarboxylic acid, dimethyl ester, 5-dimethyl acetal (30.31 g, 0,112 mol) and 2-amino-2,3-dimethylbutyramide (14.67 g, 0,113 mol) in toluene, the reaction mixture exotherms to about 40° C. The reaction mixture is heated at 80° C. for 1 hour, cooled to room temperature and diluted with water. The layers are separated and the aqueous solution is acidified to pH 3.0 with concentrated hydrochloric acid. The aqueous solution is then extracted with methylene chloride and the combined methylene chloride extracts are dried over anhydrous magnesium sulfate and concentrated in vacuo to give the title compound as a tan solid, (32.12 g, 85%), mp 135°–139° C., identified by IR and NMR spectral analyses.

EXAMPLE 13

Preparation of Dimethyl 6-chloro-5-(1,3-dioxolan-2-yl)-2,3-pyridinedicarboxylate

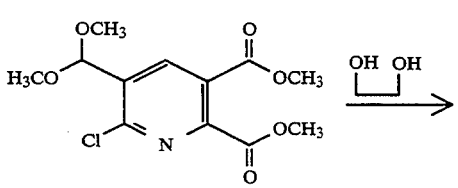

-continued

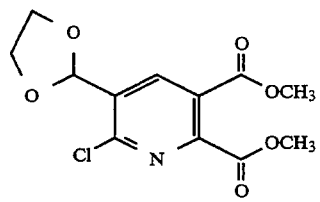

Ethylene glycol (14.3 mL, 0.255 mol), and a catalytic amount of p-toluenesulfonic acid monohydrate is added to a solution of 6-chloro-5-formyl-2,3-pyridinedicarboxylic acid, dimethyl ester, 5-(dimethyl acetal) (15.46 g, 0.051 mol) and toluene. The reaction mixture is heated at reflux temperature for 3 hours then cooled to room temperature. Ether is added and the mixture is washed with saturated sodium bicarbonate solution, dried over anhydrous magnesium sulfate and concentrated in vacuo to give the title compound as an orange oil (14.27 g, 93%), identified by IR and NMR spectral analyses.

EXAMPLE 14

Preparation of Dimethyl 5-(1,3-dioxolan-2-yl)-2,3-pyridinedicarboxylate

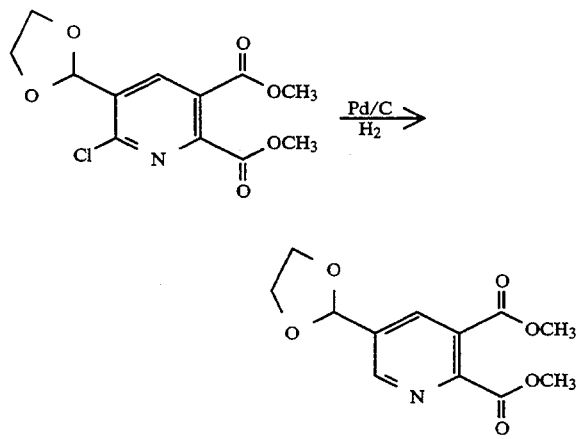

A solution of 6-chloro-5-(1,3-dioxolan-2-yl)-2,3-pyridinecarboxylic acid, dimethyl ester (9.16 g, 0.03 mol) in deoxygenated methanol is added to a Parr flask containing wet palladium on activated carbon and sodium acetate. The flask is placed in a hydrogenator where the reaction mixture absorbs hydrogen. The reaction mixture is then filtered through diatomaceous earth and the flask and diatomaceous earth are rinsed with methanol. The filtrate is concentrated in vacuo and the residual oil is partitioned between methylene chloride and water. The layers are separated and the organic layer is washed with saturated sodium bicarbonate solution, dried over anhydrous magnesium sulfate and concentrated in vacuo to give the title compound as an orange oil (3.53 g, 44%), identified by IR and NMR spectral analyses.

EXAMPLE 15

Preparation of Dimethyl 5-(1,3-Dioxepan-2-yl)-2,3-pyridinedicarboxylate

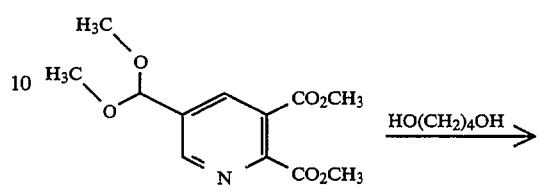

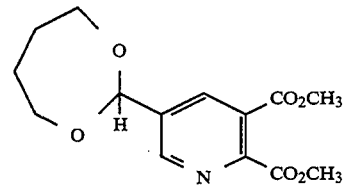

A solution of 5-formyl-2,3-pyridinedicarboxylic acid, dimethyl ester, 5-dimethyl acetal (1.3 g, 0.0048 mol), a catalytic amount of p-toluenesulfonic acid, 1,4-butanediol and toluene is heated at reflux temperature for 2 hours and 30 minutes. The reaction mixture is cooled to room temperature, made basic with sodium bicarbonate and concentrated in vacuo to give a liquid. The liquid is partitioned between methylene chloride and 5% sodium bicarbonate solution. The layers are separated and the aqueous layer is extracted with methylene chloride, the combined methylene chloride extracts are dried over anhydrous magnesium sulfate and concentrated in vacuo to give an oil. The oil is chromatographed using silica gel and hexanes/ethyl acetate (2:1 to 1:1) as eluant to give the title compound as a clear oil (0.88 g, 62%), identified by IR and NMR spectral analyses.

Following the above procedure and employing the appropriately substituted 2,3-pyridinecarboxylic acid, dimethyl ester and the appropriate diol or 2-mercaptoethanol, the compounds shown below are obtained.

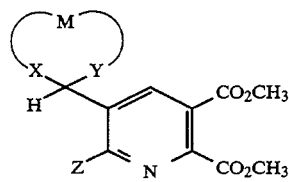

| X | Y | M | Z |
|---|---|---|---|
| O | O | C4H8 | H |
| S | O | C2H4 | H |
| O | O | C2H4 | OCH3 |
| O | O | C2H4 | CH3 |

EXAMPLE 16

Preparation of Dimethyl 5-(1,2-dimethyl-3-diaziridinyl-2,3-pyridinedicarboxylate

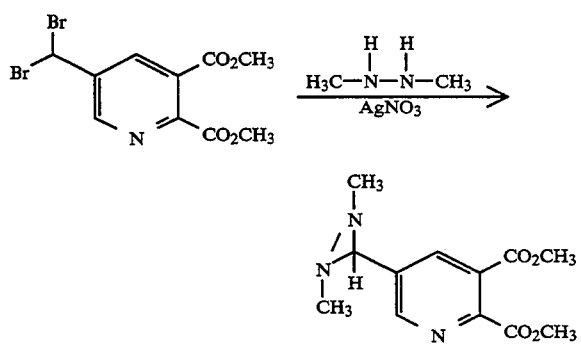

5-(Dibromomethyl)-2,3-pyridinedicarboxylic acid, dimethyl ester (2.0 g, 0.00545 mol), silver nitrate (1.85 g, 0.0109 mol) and 1,2-dimethylhydrazine dihydrochloride salt in pyridine is heated from 25° C. to 100° C. over 50 minutes, then at 100° C. for 1 hour and 45 minutes. Concentration in vacuo gives a liquid that is triturated with water and methylene chloride and filtered. The layers are separated and the aqueous layer is extracted with methylene chloride. The combined methylene chloride extracts are dried over anhydrous magnesium sulfate and concentrated in vacuo to give an oil. The oil is chromatographed using silica gel and hexanes/ethyl acetate (2:1 to 4:3 to 1:1) as eluant to give the title compound as a yellow oil (0.48 g, 33%), identified by IR and NMR spectral analyses.

EXAMPLE 17

Preparation of Dimethyl 5-(1,3-dithiolan-2-yl)-2,3-pyridinedicarboxylate

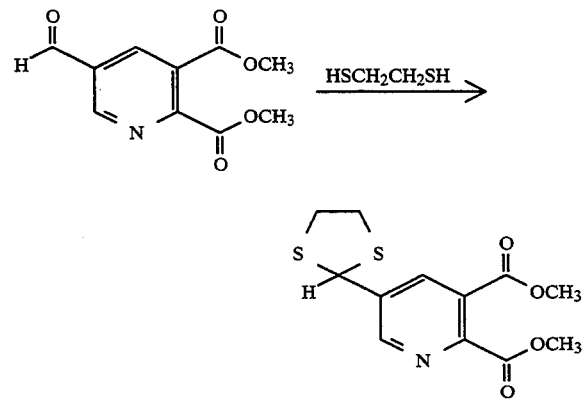

A solution of dimethyl 5-formylpyridine-2,3-dicarboxylate (0.73 g, 0.00327 mol), ethanedithiol (0.357 mL, 0.00425 mol) and a catalytic amount of para-toluenesulfonic acid in chloroform (20 mL) is heated at reflux for 5.5 hours. During this time, water is removed by placement of an addition funnel containing 3 angstrom molecular sieves in between the reaction flask and the reflux condensor. After cooling, the reaction is diluted with methylene chloride (20 mL) and is washed with 10% aqueous sodium carbonate and saturated sodium chloride solutions. The organic solution is dried over anhydrous magnesium sulfate and concentrated in vacuo to give a residue. The residue is purified by chromatography using silica gel and 33% ethyl acetate in hexanes as eluant to yield the title compound as a clear oil (0.66 g, 67%), identified by IR and NMR spectral analyses.

EXAMPLE 18

Preparation of Dimethyl 5-(1-acetyl-3-methyl-2-imidazolidinyl)pyridine-2,3-dicarboxylate

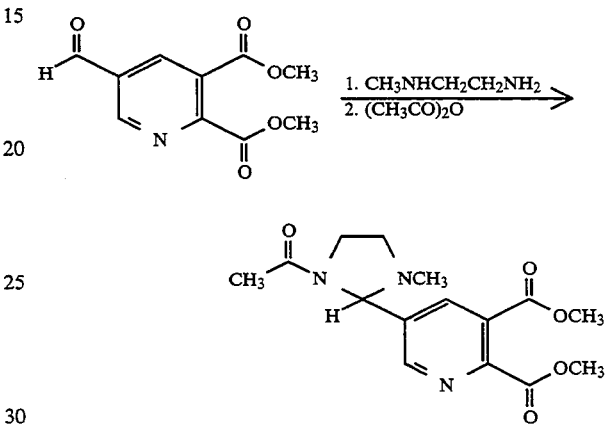

A solution of dimethyl 5-formylpyridine-2,3-dicarboxylate (0.75 g, 0.0036 mol), N-methylethylene diamine (0.38 mL, 0.0044 mol) and a catalytic amount of para-toluenesulfonic acid in toluene (10 mL) is heated at reflux temperature for 3 hours. During this process, water is removed by placement of an addition funnel containing 3 angstrom molecular sieves between the reaction flask and the reflux condensor. The reaction mixture is concentrated in vacuo, dissolved in methylene chloride (30 mL) and is washed with saturated aqueous sodium bicarbonate solution. The organic solution is dried over anhydrous magnesium sulfate and concentrated in vacuo to give a residue. The residue is dissolved in pyridine (10 mL) at 0° C. and treated with acetic anhydride (0.34 mL, 0.0036 mol). The reaction mixture is stirred for 1 hour at 0° C. and for 66 hours at room temperature. The pyridine is removed in vacuo to yield an oil. The oil is dissolved in methylene chloride and washed with saturated aqueous sodium bicarbonate. The organic solution is dried over anhydrous magnesium sulfate, concentrated in vacuo and purified by chromatography using silica gel and 10% triethylamine in ethyl acetate as eluant to yield the title compound (0.66 g, 56%) as a yellow oil, identified by IR and NMR spectral analyses.

Using the above procedure and substituting the appropriate diamine or amino alcohol add the appropriate acylating reagent, the following compounds are obtained.

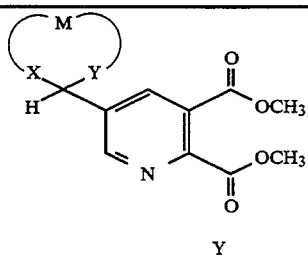

| X | Y | M |
|---|---|---|

| | | |
|---|---|---|
| NCOCH₃ | NCH₃ | (CH₂)₂ |
| NCOCH₃ | O | (CH₂)₂ |
| NCO₂CH₃ | O | (CH₂)₂ |
| NCO₂CH₂CH₃ | O | (CH₂)₂ |
| NCON(CH₃)₂ | O | (CH₂)₂ |
| NCONHCH(CH₃)₂ | O | (CH₂)₂ |
| NCOCH(CH₃)₂ | O | (CH₂)₂ |
| NCO₂CH₂CH₃ | O | (CH₂)₃ |
| NSO₂CH₃ | O | (CH₂)₂ |

Using the methods described above, the following formula I compounds may be prepared.

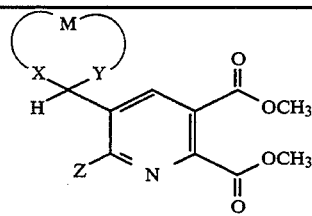

(I)

| X | Y | M | Z | mp °C. |
|---|---|---|---|---|
| O | O | (CH₂)₂ | H | oil |
| O | O | CH(CH₃)CH₂ | H | oil |
| O | O | C(CH₃)₂CH₂ | H | |
| O | O | CH(CH₃)CH(CH₃) | H | |
| O | O | (CH₂)₃ | H | oil |
| O | O | CH(CH₃)CH₂CH₂ | H | |
| O | O | CH₂CH(CH₃)CH₂ | H | |
| O | O | C(CH₃)₂CH₂CH₂ | H | |
| O | O | CH(CH₃)CH(CH₃)CH₂ | H | |
| O | O | CH₂C(CH₃)₂CH₂ | H | oil |
| O | O | (CH₂)₄ | H | oil |
| O | O | CH(CH₃)CH₂CH₂CH₂ | H | |
| O | O | CH₂CH(CH₃)CH₂CH₂ | H | |
| O | O | C(CH₃)₂CH₂CH₂CH₂ | H | |
| O | O | CH(CH₃)CH(CH₃)CH₂CH₂ | H | |
| O | O | CH(CH₃)CH₂CH₂CH(CH₃) | H | |
| O | O | CH₂C(CH₃)CH₂CH₂ | H | |
| O | O | CH₂CH(CH₃)CH(CH₃)CH₂ | H | |
| O | O | (CH₂)₅ | H | |
| O | O | CH₂CH₂OCH₂CH₂ | H | |
| O | O | CH₂CH₂OCH₂CH₂ | H | |
| O | O | CH₂CHClCH₂ | H | |
| O | O | CH₂CH(OCH₃)CH₂ | H | |
| O | S | (CH₂)₂ | H | oil |
| O | S | CH(CH₃)CH₂ | H | |
| O | S | C(CH₃)₂CH₂ | H | |
| O | S | CH(CH₃)CH(CH₃) | H | |
| O | S | (CH₂)₃ | H | |
| O | S | CH(CH₃)CH₂CH₂ | H | |
| O | S | CH₂CH(CH₃)CH₂ | H | |
| O | S | C(CH₃)₂CH₂CH₂ | H | |
| O | S | CH(CH₃)CH(CH₃)CH₂ | H | |
| O | S | CH(CH₃)CH₂CH(CH₃) | H | |
| O | S | CH₂C(CH₃)₂CH₂(CH₃) | H | |
| O | S | (CH₂)₄ | H | |
| O | S | CH(CH₃)CH₂CH₂CH₂ | H | |
| O | S | CH₂CH(CH₃)CH₂CH₂ | H | |
| O | S | C(CH₃)₂CH₂CH₂CH₂ | H | |
| O | S | CH(CH₃)CH(CH₃)CH₂CH₂ | H | |
| O | S | CH(CH₃)CH₂CH(CH₃)CH₂ | H | |
| O | S | CH(CH₃)CH₂CH₂CH(CH₃) | H | |
| O | S | CH₂C(CH₃)₂CH₂CH₂ | H | |
| O | S | CH₂CH(CH₃)CH(CH₃)CH₂ | H | |
| O | S | (CH₂)₅ | H | |
| O | S | CH₂CH₂OCH₂CH₂ | H | |
| O | S | CH₂CH₂OCH₂CH₂ | H | |
| S | S | (CH₂)₂ | H | |
| S | S | CH(CH₃)CH₂ | H | |
| S | S | C(CH₃)₂CH₂ | H | |
| S | S | CH(CH₃)CH(CH₃) | H | |
| S | S | (CH₂)₃ | H | |
| S | S | CH(CH₃)CH₂CH₂ | H | |
| S | S | CH₂CH(CH₃)CH₂ | H | |
| S | S | C(CH₃)₂CH₂CH₂ | H | |
| S | S | CH(CH₃)CH(CH₃)CH₂ | H | |

-continued

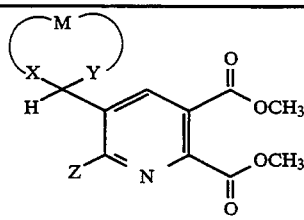

(I)

| X | Y | M | Z | mp °C. |
|---|---|---|---|---|
| S | S | CH(CH$_3$)CH$_2$CH(CH$_3$) | H | |
| S | S | CH$_2$C(CH$_3$)$_2$CH$_2$ | H | |
| S | S | (CH$_2$)$_4$ | H | |
| S | S | CH(CH$_3$)CH$_2$CH$_2$CH$_2$ | H | |
| S | S | CH$_2$CH(CH$_3$)CH$_2$CH$_2$ | H | |
| S | S | C(CH$_3$)$_2$CH$_2$CH$_2$CH$_2$ | H | |
| S | S | CH(CH$_3$)CH(CH$_3$)CH$_2$CH$_2$ | H | |
| S | S | CH(CH$_3$)CH$_2$CH(CH$_3$)CH$_2$ | H | |
| S | S | CH(CH$_3$)CH$_2$CH$_2$CH(CH$_3$) | H | |
| S | S | CH$_2$C(CH$_3$)$_2$CH$_2$CH$_2$ | H | |
| S | S | CH$_2$CH(CH$_3$)CH(CH$_3$)CH$_2$ | H | |
| S | S | (CH$_2$)$_5$ | H | |
| S | S | CH$_2$CH$_2$OCH$_2$CH$_2$ | H | |
| S | S | CH$_2$CH$_2$OCH$_2$CH$_2$ | H | |
| O | O | (CH$_2$)$_2$ | CH$_3$ | oil |
| O | O | (CH$_2$)$_2$ | CH$_2$CH$_3$ | |
| O | O | (CH$_2$)$_2$ | CH(CH$_3$)$_2$ | |
| O | O | (CH$_2$)$_2$ | CH$_2$CH$_2$CH$_3$ | |
| O | O | CH(CH$_3$)CH$_2$ | CH$_3$ | |
| O | O | C(CH$_3$)$_2$CH$_2$ | CH$_3$ | |
| O | O | (CH$_2$)$_3$ | CH$_3$ | |
| O | O | (CH$_2$)$_4$ | CH$_3$ | |
| O | S | (CH$_2$)$_2$ | CH$_3$ | |
| O | S | (CH$_2$)$_2$ | CH$_2$CH$_3$ | |
| O | S | (CH$_2$)$_2$ | CH(CH$_3$)$_2$ | |
| O | S | (CH$_2$)$_2$ | CH$_2$CH$_2$CH$_3$ | |
| O | S | CH(CH$_3$)CH$_2$ | CH$_3$ | |
| O | S | C(CH$_3$)$_2$CH$_2$ | CH$_3$ | |
| O | S | (CH$_2$)$_3$ | CH$_3$ | |
| O | S | (CH$_2$)$_4$ | CH$_3$ | |
| S | S | (CH$_2$)$_2$ | CH$_3$ | |
| S | S | (CH$_2$)$_2$ | CH$_2$CH$_3$ | |
| S | S | (CH$_2$)$_2$ | CH(CH$_3$)$_2$ | |
| S | S | (CH$_2$)$_2$ | CH$_2$CH$_2$CH$_3$ | |
| S | S | CH(CH$_3$)CH$_2$ | CH$_3$ | |
| S | S | C(CH$_3$)$_2$CH$_2$ | CH$_3$ | |
| S | S | (CH$_2$)$_3$ | CH$_3$ | |
| S | S | (CH$_2$)$_4$ | CH$_3$ | |
| O | O | (CH$_2$)$_2$ | OCH$_3$ | oil |
| O | O | (CH$_2$)$_2$ | OCH$_2$CH$_3$ | |
| O | O | (CH$_2$)$_2$ | OCH(CH$_3$)$_2$ | |
| O | O | CH(CH$_3$)CH$_2$ | OCH$_3$ | |
| O | O | (CH$_2$)$_3$ | OCH$_3$ | |
| O | O | (CH$_2$)$_4$ | OCH$_3$ | |
| O | O | (CH$_2$)$_2$ | Cl | oil |
| O | O | (CH$_2$)$_2$ | Br | |
| O | O | (CH$_2$)$_2$ | F | |
| O | O | CH(CH$_3$)CH$_2$ | Cl | |
| O | O | CH(CH$_3$)CH$_2$ | Br | |
| O | O | CH(CH$_3$)CH$_2$ | F | |
| O | O | (CH$_2$)$_3$ | Cl | |
| O | O | (CH$_2$)$_3$ | Br | |
| O | O | (CH$_2$)$_3$ | F | |
| O | O | (CH$_2$)$_4$ | Cl | |
| O | O | (CH$_2$)$_4$ | Br | |
| O | O | (CH$_2$)$_4$ | F | |
| S | S | (CH$_2$)$_2$ | OCH$_3$ | |
| S | S | (CH$_2$)$_2$ | OCH$_2$CH$_3$ | |
| S | S | (CH$_2$)$_2$ | OCH(CH$_3$)$_2$ | |
| S | S | CH(CH$_3$)CH$_2$ | OCH$_3$ | |
| S | S | (CH$_2$)$_3$ | OCH$_3$ | |
| S | S | (CH$_2$)$_4$ | OCH$_3$ | |
| S | S | (CH$_2$)$_2$ | Cl | |
| S | S | (CH$_2$)$_2$ | Br | |
| S | S | (CH$_2$)$_2$ | F | |
| S | S | CH(CH$_3$)CH$_2$ | Cl | |
| S | S | CH(CH$_3$)CH$_2$ | Br | |
| S | S | CH(CH$_3$)CH$_2$ | F | |
| S | S | (CH$_2$)$_3$ | Cl | |

-continued

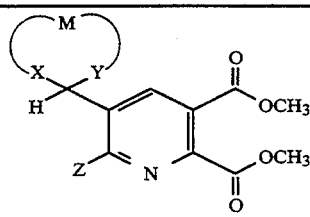

(I)

| X | Y | M | Z | mp °C. |
|---|---|---|---|---|
| S | S | (CH$_2$)$_3$ | Br | |
| S | S | (CH$_2$)$_3$ | F | |
| S | S | (CH$_2$)$_4$ | Cl | |
| S | S | (CH$_2$)$_4$ | Br | |
| S | S | (CH$_2$)$_4$ | F | |
| O | S | (CH$_2$)$_2$ | OCH$_3$ | |
| O | S | (CH$_2$)$_2$ | OCH$_2$CH$_3$ | |
| O | S | (CH$_2$)$_2$ | OCH(CH$_3$)$_2$ | |
| O | S | CH(CH$_3$)CH$_2$ | OCH$_3$ | |
| O | S | (CH$_2$)$_3$ | OCH$_3$ | |
| O | S | (CH$_2$)$_4$ | OCH$_3$ | |
| O | S | (CH$_2$)$_2$ | Cl | |
| O | S | (CH$_2$)$_2$ | Br | |
| O | S | (CH$_2$)$_2$ | F | |
| O | S | CH(CH$_3$)CH$_2$ | Cl | |
| O | S | CH(CH$_3$)CH$_2$ | Br | |
| O | S | CH(CH$_3$)CH$_2$ | F | |
| O | S | (CH$_2$)$_3$ | Cl | |
| O | S | (CH$_2$)$_3$ | Br | |
| O | S | (CH$_2$)$_3$ | F | |
| O | S | (CH$_2$)$_4$ | Cl | |
| O | S | (CH$_2$)$_4$ | Br | |
| O | S | (CH$_2$)$_4$ | F | |
| NCH$_3$ | O | (CH$_2$)$_2$ | H | oil |
| NCH$_2$CH$_3$ | O | (CH$_2$)$_2$ | H | |
| NCH$_3$ | O | (CH$_2$)$_3$ | H | |
| NCH$_3$ | O | (CH$_2$)$_4$ | H | |
| NCOCH$_3$ | O | (CH$_2$)$_2$ | H | oil |
| NCOCH$_3$ | O | (CH$_2$)$_3$ | H | |
| NCOCH$_3$ | O | (CH$_2$)$_4$ | H | |
| NCOCH$_2$CH$_3$ | O | (CH$_2$)$_2$ | H | |
| NCOCH(CH$_3$)$_2$ | O | (CH$_2$)$_2$ | H | oil |
| NCO$_2$CH$_3$ | O | (CH$_2$)$_2$ | H | oil |
| NCO$_2$CH$_3$ | O | CH(CH$_3$)CH$_2$ | H | |
| NCO$_2$CH$_3$ | O | (CH$_2$)$_3$ | H | |
| NCO$_2$CH$_3$ | O | (CH$_2$)$_4$ | H | |
| NCO$_2$CH$_2$CH$_3$ | O | (CH$_2$)$_2$ | H | oil |
| NCO$_2$CH(CH$_3$)$_2$ | O | (CH$_2$)$_2$ | H | |
| NCON(CH$_3$)$_2$ | O | (CH$_2$)$_2$ | H | oil |
| NCON(CH$_3$)$_2$ | O | (CH$_2$)$_3$ | H | |
| NCON(CH$_3$)$_2$ | O | (CH$_2$)$_4$ | H | |
| NCON(CH$_2$CH$_3$)$_2$ | O | (CH$_2$)$_2$ | H | |
| NCONHCH$_3$ | O | (CH$_2$)$_2$ | H | |
| NCONHCH$_2$CH$_3$ | O | (CH$_2$)$_2$ | H | |
| NCONHCH$_2$CH$_2$CH$_3$ | O | (CH$_2$)$_2$ | H | |
| NCONHCH(CH$_3$)$_2$ | O | (CH$_2$)$_2$ | H | oil |
| NCO$_2$CH$_2$CH$_3$ | O | (CH$_2$)$_3$ | H | oil |
| NCO$_2$CH$_2$CH$_3$ | O | (CH$_2$)$_4$ | H | |
| NCH$_3$ | NCOCH$_3$ | COCH$_2$ | H | |
| NCH$_3$ | NCO$_2$CH$_3$ | COCH$_2$ | H | |
| NCH$_3$ | NCON(CH$_3$)$_2$ | COCH$_2$ | H | |
| NCH$_2$CH$_3$ | NCOCH$_3$ | COCH$_2$ | H | |
| NCH$_2$CH$_3$ | NCO$_2$CH$_3$ | COCH$_2$ | H | |
| NCH$_2$CH$_3$ | NCO$_2$CH$_3$ | COCH$_2$ | H | |
| O | NCOCH$_3$ | COCH$_2$ | H | |
| O | NCOCH$_2$CH$_3$ | COCH$_2$ | H | |
| O | NCO$_2$CH$_3$ | COCH$_2$ | H | |
| O | NCO$_2$CH$_2$CH$_3$ | COCH$_2$ | H | |
| O | NCON(CH$_3$)$_2$ | COCH$_2$ | H | |
| O | NCON(CH$_2$CH$_3$)$_2$ | COCH$_2$ | H | |
| NCH$_3$ | NCOCH$_3$ | COCH(CH$_3$) | H | |
| NCH$_3$ | NCO$_2$CH$_3$ | COCH(CH$_3$) | H | |
| NCH$_3$ | NCON(CH$_3$)$_2$ | COCH(CH$_3$) | H | |
| O | NCOCH$_3$ | COCH(CH$_3$) | H | |
| O | NCO$_2$CH$_3$ | COCH(CH$_3$) | H | |
| O | NCON(CH$_3$)$_2$ | COCH(CH$_3$) | H | |
| NCH$_3$ | O | COCH$_2$ | H | |
| NCH$_3$ | O | COCH$_2$CH$_2$ | H | |
| NCH$_3$ | O | COCH(CH$_3$) | H | |

-continued

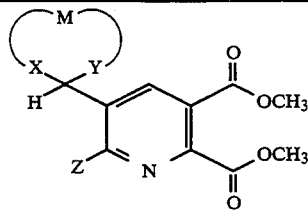

(I)

| X | Y | M | Z | mp °C. |
|---|---|---|---|---|
| NCH₃ | NCH₃ | COCO | H | |
| NCH₃ | NCH₃ | COCH₂CO | H | |
| NCH₃ | O | COCO | H | |
| NCH₃ | O | COCH₂CO | H | |
| NCH₃ | NCH₃ | — | CH₃ | |
| NCH₂CH₃ | NCH₃ | — | CH₃ | |
| NCH₂CH₃ | NCH₂CH₃ | — | CH₃ | |
| NCH₃ | NH | (CH₂)₂ | CH₃ | |
| NCH₃ | NCOCH₃ | (CH₂)₂ | CH₃ | |
| NCH₃ | NCOCH₂CH₃ | (CH₂)₂ | CH₃ | |
| NCH₃ | NCOCH₃ | (CH₂)₃ | CH₃ | |
| NCH₃ | NCO₂CH₃ | (CH₂)₂ | CH₃ | |
| NCH₃ | NCO₂CH₃ | (CH₂)₃ | CH₃ | |
| NCH₃ | NCOCH₃ | (CH₂)₃ | CH₃ | |
| NCH₃ | NCOCH₃ | (CH₂)₄ | CH₃ | |
| NCH₃ | S | (CH₂)₂ | CH₃ | |
| NCH₃ | S | (CH₂)₃ | CH₃ | |
| NCH₃ | S | (CH₂)₄ | CH₃ | |
| NCOCH₃ | S | (CH₂)₂ | CH₃ | |
| NCO₂CH₃ | S | (CH₂)₃ | CH₃ | |
| NCH₃ | NCH₃ | — | H | |
| NCH₂CH₃ | NCH₃ | — | H | |
| NCH₂CH₃ | NCH₂CH₃ | — | H | |
| NCH₃ | NH | (CH₂)₂ | H | |
| NCH₃ | NCOCH₃ | (CH₂)₂ | H | |
| NCH₃ | NCOCH₂CH₃ | (CH₂)₂ | H | |
| NCH₃ | NCOCH₃ | (CH₂)₃ | H | |
| NCH₃ | NCO₂CH₃ | (CH₂)₂ | H | |
| NCH₃ | NCO₂CH₃ | (CH₂)₃ | H | |
| NCH₃ | NCOCH₃ | (CH₂)₃ | H | |
| NCH₃ | NCO₂CH₃ | (CH₂)₄ | H | |
| NCH₃ | NCOCH₃ | (CH₂)₄ | H | |
| NCH₃ | S | (CH₂)₂ | H | |
| NCH₃ | S | (CH₂)₃ | H | |
| NCH₃ | S | (CH₂)₄ | H | |
| NCOCH₃ | S | (CH₂)₂ | H | |
| NCO₂CH₃ | S | (CH₂)₃ | H | |
| O | O | COCH₂ | H | |
| O | O | COCH₂CH₂ | H | |
| O | O | COCH₂CH(CH₃) | H | |
| O | O | COCO | H | |
| O | O | COCH₂CO | H | |
| O | O | COCH=CH | H | |
| O | O | COCH=C(CH₃) | H | |
| O | O | CH=CH | H | |
| O | O | CH=CHCH₂ | H | |
| O | O | (CH₃)C=CHCH₂ | H | |
| O | O | CH=CHCH(CH₃) | H | |
| O | S | COCH₂ | H | |
| O | O | CH₂CH(CO₂CH₃) | H | |

EXAMPLE 19

Preparation of
5-(1,3-Dioxolan-2-yl)-2,3-pyridinedicarboxylic acid

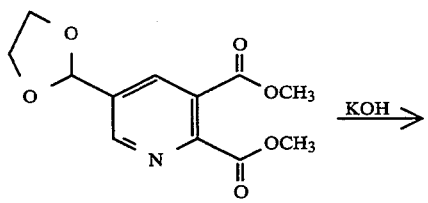 $\xrightarrow{\text{KOH}}$

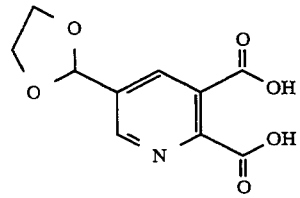

5-(1,3-Dioxolan-2-yl)-2,3-pyridinedicarboxylic acid, dimethyl ester (2.86 g, 0.011 mol) in methanol is added dropwise to a mixture of potassium hydroxide (1.26 g, 0.022 mol) and methanol. The reaction mixture is heated for 3 hours and 30 minutes at about 62° C., cooled to room temperature, acidified to pH 1 with concentrated hydrochloric acid, filtered through diatomaceous earth and the filtrate is concentrated in vacuo to yield the title compound as a pale yellow powder (2.86 g, 100%), identified by IR and NMR spectral analyses.

EXAMPLE 20

Preparation of 5-(1,3-Dioxolan-2-yl)-2,3,pyridinedicarboxylic acid

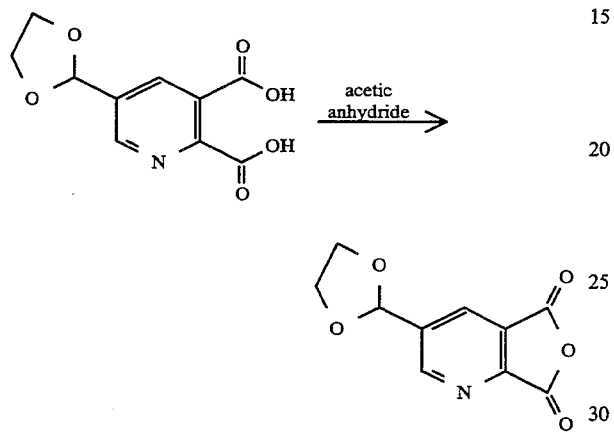

A solution of 5-(1,3-dioxolan-2-yl)-2,3-pyridinedicarboxylic acid (2.86 g, 0.012 mol), acetic anhydride (11.3 mL, 0.12 mol) and pyridine is stirred at room temperature for 1 hour and 45 minutes, then at reflux temperature for 4 hours. The reaction mixture is concentrated in vacuo to give the title compound as an oil (2.64 g, 100%), identified by IR spectra analysis.

EXAMPLE 21

Preparation of 2-[(1-Carbamoyl-1,2-dimethylpropyl)-carbamoyl]-5-(1,3-dioxolan-2-yl)nicotinic acid

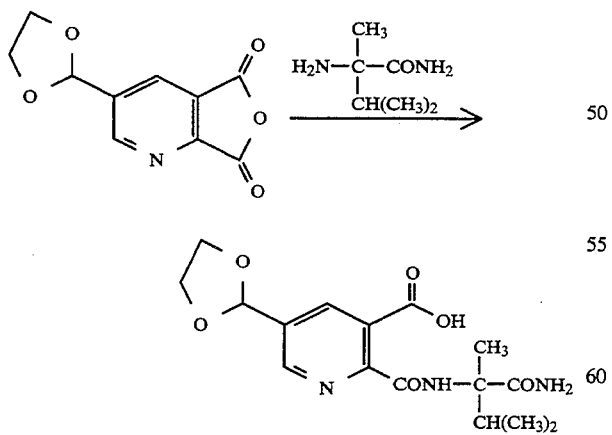

A solution of 5-(1,3-dioxolan-2-yl)-2,3-pyridinedicarboxylic anhydride (2.64 g, 0.012 mol) and 2-amino-2,3-dimethylbutyramide (1.55 g, 0.012 mol) in tetrahydrofuran is stirred for 2 days at room temperature. The reaction mixture is concentrated in vacuo to give the title compound as an orange oil (5.4 g, 100%), identified by NMR spectra analysis.

EXAMPLE 22

Preparation of 5-(1,3-Dioxolan-2-yl)-2-(4-isopropyl-4-methyl-5-oxo-2-imidazolin-2-yl)nicotinic acid

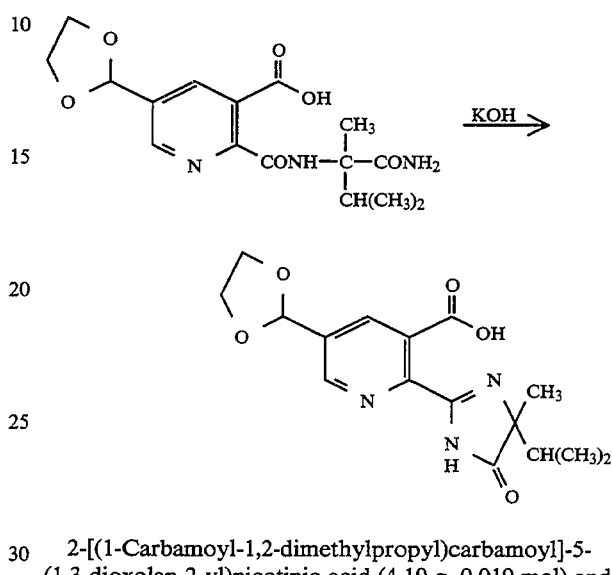

2-[(1-Carbamoyl-1,2-dimethylpropyl)carbamoyl]-5-(1,3-dioxolan-2-yl)nicotinic acid (4.19 g, 0.019 mol) and 15% potassium hydroxide is heated at 80° C. for 1 hour. The reaction mixture is acidified to pH 3 with concentrated hydrochloric acid and methylene chloride is added. The methylene chloride layer is separated, dried over anhydrous magnesium sulfate and concentrated in vacuo to give an oil. The oil is chromatographed using silica gel and methylene chloride with increasing percentage of ether as eluent to give the title compound as a pale yellow solid (0.19 g, 5%), mp 156° C., identified by IR and NMR spectral analyses.

EXAMPLE 23

Preparation of 5-(-1,3-Dioxepan-2-yl)-2-(4-isopropyl-4-methyl-5-oxo-2-imidazolin-2-yl)nicotinic acid

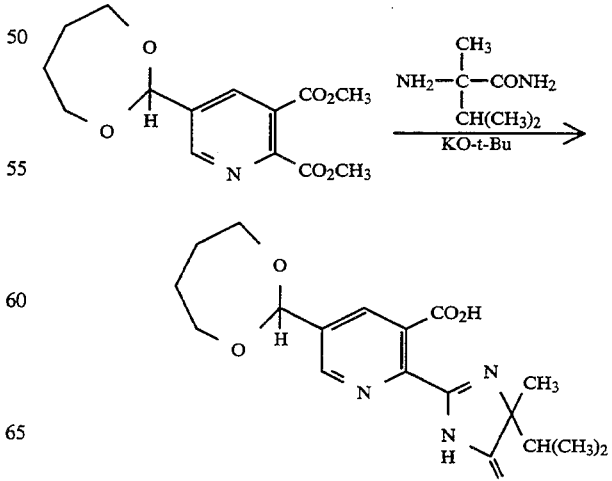

5-(1,3-Dioxepan-2-yl)-2,3-pyridinedicarboxylic acid, dimethyl ester (0.9 g, 0.00305 mol) in toluene is added to 2-amino-2,3-dimethylbutyramide (0.4 g, 0.00305 mol) and potassium tert-butoxide (0.69 g, 0.0061 mol) in toluene. The mixture is heated for 3 hours from 60° to 70° C. The reaction mixture is cooled to room temperature, water is added and the mixture is concentrated in vacuo to give an oil. The oil is diluted with water and washed with ether. The aqueous solution is acidified to pH 3.1 with 2 normal hydrochloric acid solution and extracted with methylene chloride. The combined methylene chloride extracts are dried over anhydrous magnesium sulfate and concentrated in vacuo to give the title compound as a white solid (0.63 g, 57%) mp 60°–69° C., identified by IR and NMR spectral analyses.

Following the above procedure and substituting the appropriate formula I 2,3-pyridinedicarboxylate, the following formula II compounds are obtained.

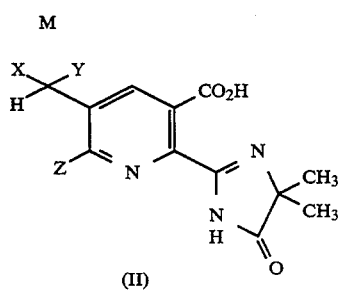

(II)

| X | Y | M | Z | mp °C. |
|---|---|---|---|---|
| O | O | (CH₂)₄ | H | 60–69 |
| S | O | (CH₂)₂ | H | 72–76 |
| NCH₃ | NCH₃ | — | H | 174–176 |
| O | O | (CH₂)₂ | CH₃ | 75 |
| O | O | (CH₂)₂ | OCH₃ | 222–223 |
| O | O | (CH₂)₂ | Cl | 79–80 |
| S | S | (CH₂)₂ | H | 125–133 |
| O | NCO₂CH₃ | (CH₂)₂ | H | 178–180 |
| O | NCO₂CH₂CH₃ | (CH₂)₂ | H | 75–77 |
| O | NCOCH₃ | (CH₂)₂ | H | 167–168 |
| O | NCON(CH₃)₂ | (CH₂)₂ | H | 198–199 |
| O | NCOCH(CH₃)₂ | (CH₂)₂ | H | 91–93 |
| O | NCONHCH(CH₃)₂ | (CH₂)₂ | H | 181–183 |
| O | NCO₂CH₂CH₃ | (CH₂)₃ | H | 77–79 |
| O | NSO₂CH₃ | (CH₂)₃ | H | 188–192 |

EXAMPLE 24

Preparation of
5-(1-Acetyl-3-methyl-2-imidazolidinyl)-2-(4-isopropyl-4-methyl-5-oxo-2-imidazolin-2-yl)nicotinic acid ammonium salt

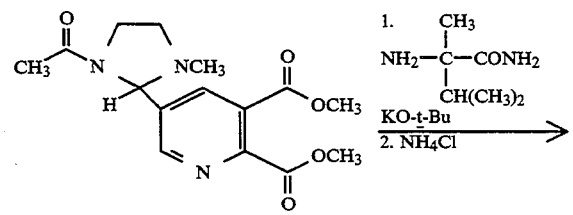

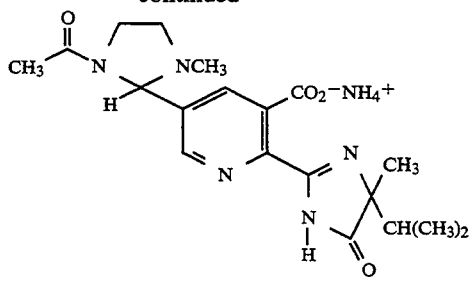

To a stirred solution of dimethyl 5-(1-acetyl-3-methyl-2-imidazolidinyl)pyridine-2,3-dicarboxylate (0.70 g, 0.0022 mol), and 2-amino-2,3-dimethylbutyramide (0.28 g, 0.0022 mol) in toluene (10 mL) is added potassium tert-butoxide (0.49 g, 0.0044 mol). The resulting mixture is stirred for 2 hours at 80° C. to 90° C. After cooling to room temperature, the reaction is quenched by the addition of water (15 mL) and ammonium chloride (0.25 g). The layers are separated, the aqueous solution concentrated under high vacuum, the product triturated with 33% ethanol in chloroform and filtered. The filtrate is concentrated in vacuo to afford the title compound (0.95 g, 100%) as a gold solid, mp 93°–98° C., identified by IR and NMR spectral analyses.

I claim:

1. A method for the preparation of a compound having the formula I structure

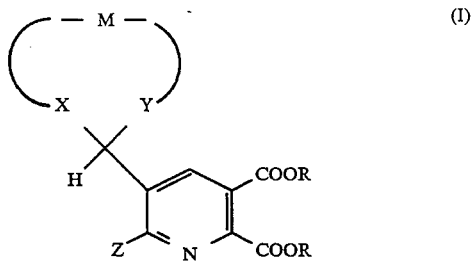

wherein

R is C₁–C₆ alkyl;

X and Y are each independently oxygen, sulfur or NR₄;

R₄ is hydrogen, C₁–C₆ alkyl optionally substituted with C₁–C₄ alkoxy or 1–3 halogens, SO₂R₅, COR₅, CO₂R₅ or CONR₅R₅;

R₅ is hydrogen, C₁–C₆ alkyl optionally substituted with 1–3 halogens, or C₂–C₆ alkenyl;

M is C₂–C₅ alkylene optionally substituted with 1 or 2 C₁–C₄ alkyl groups, C₁–C₄ alkoxy, halogen, CO₂R₆ or oxo, and optionally interrupted by one oxygen or one sulfur C₂ alkenylene optionally substituted with 1 or 2 C₁–C₄ alkyl groups or CO₂R₆, C₃ alkenylene optionally substituted with 1 or 2 C₁–C₄ alkyl groups or CO₂R₆ or oxo, methyleneamino, optionally substituted with C₁–C₄ alkyl or CO₂R₆, or a single bond, with the proviso that both X and Y are NR₄, provided that the ring formed by M, X and Y and the carbon to which they are attached is no more than 8 atoms and provided that when the substituents on M are either alkoxy or halogen the substituted carbon is not bound to X or Y;

R₆ is hydrogen, methyl or ethyl;

Z is hydrogen., halogen, $C_1$–$C_6$ alkoxy, or $C_1$–$C_6$ alkyl optionally substituted with $C_1$–$C_4$ alkoxy or halogen which comprises reacting a compound having the structure

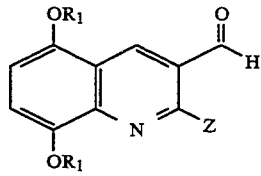

wherein $R_1$ is $C_1$–$C_4$ alkyl, with at least 2 molar equivalents of a tri($C_1$–$C_4$)alkylorthoformate in the presence of a $C_1$–$C_4$ alkyl alcohol, ozone and a catalytic amount of an acid to yield a di($C_1$–$C_4$)alkyl acetal pyridinedicarboxylate having the structure

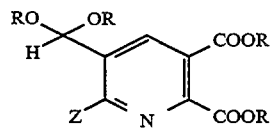

wherein R is $C_1$–$C_4$ alkyl and reacting said di($C_1$–$C_4$)alkyl acetal with at least one molar equivalent of an agent having the structure

HX—M—YH wherein X, M and Y are as described above in the presence of an acid and a solvent to give the formula I 5-heterocyclic-pyridine2,3-dicarboxylate compound.

* * * * *